(12) United States Patent
Busch et al.

(10) Patent No.: US 7,854,840 B2
(45) Date of Patent: Dec. 21, 2010

(54) METHOD FOR DECOMPOSING BIOGENIC MATERIAL

(75) Inventors: Guenter Busch, Cossebaude (DE); Marko Sieber, Forst (DE)

(73) Assignee: Brandenburgische Technische Universitaet Cottbus, Cottbus (DE)

( * ) Notice: Subject to any disclaimer, the term of this patent is extended or adjusted under 35 U.S.C. 154(b) by 373 days.

(21) Appl. No.: 11/666,909

(22) PCT Filed: Nov. 3, 2005

(86) PCT No.: PCT/DE2005/001990

§ 371 (c)(1),
(2), (4) Date: Jun. 26, 2008

(87) PCT Pub. No.: WO2006/048008

PCT Pub. Date: May 11, 2006

(65) Prior Publication Data

US 2008/0314824 A1 Dec. 25, 2008

(30) Foreign Application Priority Data

Nov. 3, 2004 (DE) ........................ 10 2004 053 615

(51) Int. Cl.
*C02F 3/30* (2006.01)

(52) U.S. Cl. .................. 210/603; 210/605; 210/622; 210/630

(58) Field of Classification Search .................. 210/603, 210/605, 612, 613, 621, 622, 630
See application file for complete search history.

(56) References Cited

U.S. PATENT DOCUMENTS

| 4,400,195 A | | 8/1983 | Rijkens | |
|---|---|---|---|---|
| 4,652,374 A | * | 3/1987 | Cohen | ................. 210/603 |
| 4,769,149 A | * | 9/1988 | Nobilet et al. | ............ 210/603 |
| 5,228,995 A | * | 7/1993 | Stover | ................... 210/603 |
| 5,269,634 A | | 12/1993 | Chynoweth et al. | |
| 6,110,727 A | | 8/2000 | Widmer et al. | |

FOREIGN PATENT DOCUMENTS

| DE | 35 45 679 A1 | 6/1987 |
|---|---|---|
| DE | 196 23 163 A1 | 12/1996 |
| DE | 198 46 336 A1 | 9/1999 |
| DE | 199 09 328 A1 | 5/2000 |
| EP | 0 659 696 A1 | 6/1995 |

* cited by examiner

*Primary Examiner*—Fred Prince
(74) *Attorney, Agent, or Firm*—Kriegsman & Kriegsman

(57) ABSTRACT

The invention relates to a method for decomposing biogenic material, wherein a percolator is charged with biogenic material, a percolation liquid is separated by sieving and re-sprayed again onto the biogenic material, excess percolation liquid is pumped into a buffer from where it is transported into a biogas reactor and fermented to form biogas. The method is characterized in that the purified percolation liquid is transferred as waste water to a storage buffer container from where it can be retransferred to the percolator.

16 Claims, 1 Drawing Sheet

METHOD FOR DECOMPOSING BIOGENIC MATERIAL

Figure 1:
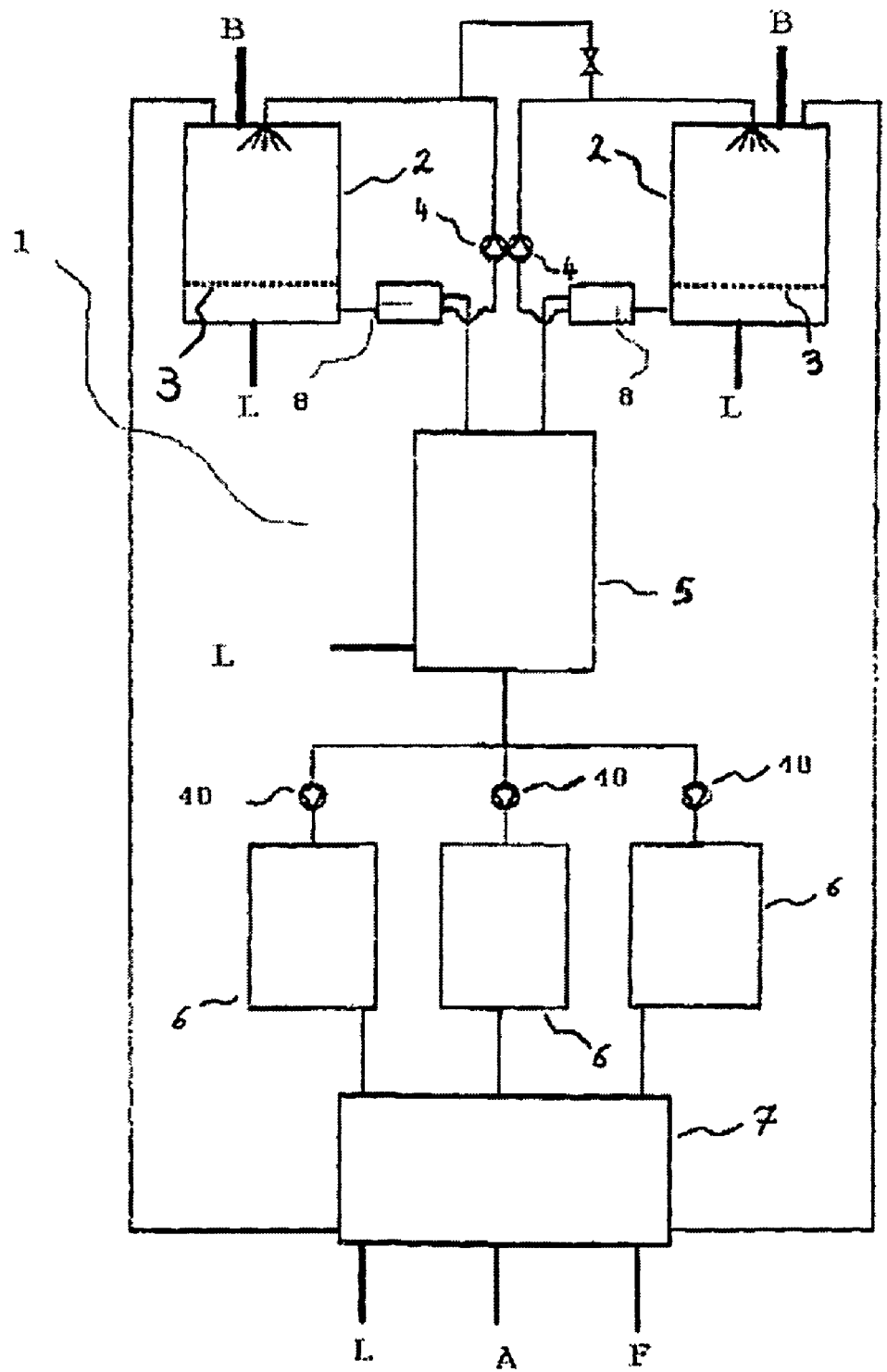

The invention relates to a method for decomposing biogenic material and a biogas plant belonging thereto as well as its use.

The fermentation of biological substances is a process that has been known for a long time. One-stage, two-stage, or multi-stage methods have been developed on the basis of the most varied developments. In addition to wet fermentation developed from liquid-manure fermentation, dry fermentation is also practiced.

The principle of two-stage dry-wet fermentation was described for the first time by Gosh, 1978. In this process, wastes are percolated in an anaerobic reactor. The percolation water is subsequently fermented to biogas in a methane reactor. The method was further developed and patented by Rijkens and Hofank (U.S. Pat. No. 4,400,195) in the 80s for organic wastes.

This method was converted twice to practice, to the ANM method in Ganderkesee and to the Prethane-Rudad method in Breda.

Wellinger and Suter also conducted tests in the 80s with solid manure and Widmer with market and meatpacking wastes. In this case, the percolator was also driven in an aerobic environment.

The newest plants, which have been developed according to this method (for residual wastes) are the ISKA® percolation method in Sansenheck and the BIOPERCOLAT® method (DE 198 46 336 A1). Here, the waste is hydrolyzed in a percolator after a mechanical pretreatment (for example, sieving, metal separation). The percolator is therefore equipped with a stirring mechanism, so that the wastes are continually transported through the reactor. After a residence time of 2 to 3 days, the percolate is discharged free of water and ready for further treatment or depositing in a layer. The percolation water is fermented anaerobically to biogas in a methane reactor after separation of sand and fibers. The water that is cleaned in this way is directly used as percolation water or is used after another cleaning (for removing nitrogen).

The object of the invention is to make possible a control of the biogas production according to need in the decomposing of biogenic material.

The object is accomplished by a decomposing method, whose features are given in the principal claim. Advantageous configurations are characterized in the dependent claims.

The object of the present invention is achieved by a decomposing method, wherein a percolator is charged with biogenic material, a percolation liquid is separated by means of a sieve and again sprayed onto the bio-genic material, excess percolation liquid is introduced into a buffer tank, from there pumped into a biogas reactor and fermented to biogas, wherein the cleaned percolation liquid is transferred as wastewater into a storage buffer tank and wherein the wastewater can be transferred from there again into the percolator.

According to the invention, it is thus a decomposing method for biogenic material with control of the amount of biogas formed according to need, wherein an aerobically driven percolator is charged with biogenic material, a percolation liquid is separated by means of a sieve and again sprayed onto the biogenic material, excess percolation liquid is introduced into a buffer tank, from there pumped into a biogas reactor and fermented to biogas, whereby the cleaned percolation liquid is transferred as wastewater into a separate storage buffer tank and can be transferred from there again into the percolator.

This decomposing method has the advantage that it is based on a simple technique for decomposing biogenic material. In this way, a control of the biogas formed according to need is made possible, and in this way, the biogas requirement, for example, for conversion to electrical energy or production of heat at peak times or times of low demand can be controlled accordingly. While the control of biogas production cannot be provided or can be provided only in constricted periods for adapting to consumption in the known plants, a rapid adaptation to the current requirement can be provided with the decomposing method according to the invention.

All substances originating from living organisms can be considered as biogenic material, in particular, the following: biowastes, lawn cuttings, industrial waste, food waste, household waste, agricultural waste, kitchen waste, renewable resources and similar materials.

The percolation liquid is preferably stored. The control of biogas formation according to need is possible for the percolation liquid by means of an appropriately dimensioned buffer tank (max. 24 h buffer), since the response time for the biogas production lies in the range of hours, due to the technical process for operating methane reactions. The function of the gas storage means can thus be replaced by the storage of the percolation liquid.

In a preferred embodiment of the invention, a shock of compressed air is impressed discontinuously through the perforated walls of a sieve bottom. In this way, obstructions of the sieve bottom can be removed or loosened and a free passage of the percolation liquid through the sieve bottom can again be assured.

Normal pressure preferably prevails in the percolator. An input of air is harmless. An air input into the percolator can occur continuously or discontinuously, independently from the shock of compressed air. It is further possible to heat the percolator. The temperature in the percolator should then amount to approximately 30° C. Advantageously, the percolator is driven aerobically.

The entire liquid in the system is pumped through one circuit. The percolation liquid leaving the bioreactor as wastewater is preferably discharged discontinuously and fresh liquid is introduced. In this way, a concentration of foreign matter in the circuit is avoided.

Substances that sink and/or float are separated in the buffer tank and/or in the storage buffer tank. This process can be conducted by using the most varied separating devices or high-power separating devices, such as, for example, centrifuges.

Fermenting to biogas is preferably conducted by means of bacteria. In this case, the fermentation is conducted with the participation of a bacterial matrix of several bacterial strains. The biogas reactor can be heated; in particular, it can be heated from the outside. In this way, a constant temperature can always be maintained in the biogas reactor. This is either approximately 37° C. or 55° C.

In addition, the invention is achieved by a biogas plant, consisting of at least one percolator with a sieve bottom and a pump, a buffer tank, at least one biogas reactor, and at least one storage buffer tank, wherein the percolator is constructed here according to the Garagen method for aerobic operation.

Preferably, the biogas plant consists of at least two parallelly connected percolators. In this case, the percolation liquid is sprayed continuously or discontinuously over the biogenic material by means of a separate pump for each percolator, each time depending on the material used. Thus, a separately operable liquid circuit is formed for each percolator. A connection between the individual percolators is possible in order to inoculate the biogenic material with specific species of bacteria.

The use of at least two percolators, in addition, has the advantage that a loading and unloading of solid materials is possible at any time. In addition, an adaptation to the respective substance formation or the energy decrease is possible due to the modular construction, and substrate-specific residence time in the percolator can be controlled individually. Due to the aerobic operation of the percolators, the formation of methane and thus an atmosphere at risk of explosion in the percolator is not possible.

In the decomposing of biogenic material, acids are formed, so that the percolators are preferably acid-resistant. The percolation liquid, however, dissolves the acids that form, as well as other materials, and the percolation liquid is enriched with materials that can be easily fermented.

It is also conceivable that an extremely acidic liquid flow is treated together with the percolation liquid in the biogas reactor. For example, in the canning industry, on the one hand, a high wastewater flow with organic loads is formed, which is strongly acidic for the most part; however, on the other hand, there is also solid waste. The annually fluctuating formation of acidic wastewater could be equilibrated with the use of solid wastes as needed, so that at times when there is little formation of wastewater, a good biogas production can still be carried out.

Also, preferably, the percolators have a sieve bottom. The latter serves for the purpose of conducting a solid-liquid separation. The separated percolation liquid collects at the bottom or under the sieve bottom and is sprayed continuously or discontinuously in the circuit over the biogenic material by means of pumps. Excess percolation liquid is pumped into the buffer tank with appropriate filling level and from there into the biogas reactor.

The temperature in the percolator should amount to approximately 30° C.; therefore, the percolators preferably can be heated.

It is preferred according to the invention that the fermenting to biogas is provided by means of added and/or immobilized bacteria.

The biogas reactor is essentially gas-tight and functions according to a reactor principle that is common for wastewater technology (UASB-sludge bed [upflow anaerobic sludge bed], solid bed reactor).

A solid bed biogas reactor can be operated as a plug flow reactor (filter), so that both the residence time in the percolator as well as the residence time in the biogas reactor can be defined.

Biogas consists of methane ($CH_4$) [50-85 vol. %], carbon dioxide ($CO_2$) [15-50 vol. %] as well as oxygen, nitrogen and trace gases (including hydrogen sulfide). A biogas with a high methane fraction of between 65 and 80 vol. % is produced with the decomposing method according to the invention. Among other things, it can be used directly for heating purposes or, by means of a block-type thermal power system, for the coupled production of electricity and heat. The gas is produced by anaerobic fermentation of organic substances.

In order to increase the biogas yield, frequently co-fermentates (for example, renewable resources or wastes from the food industry) are used. The fermented organic material can subsequently be evaluated as high-value fertilizer for agricultural use.

After the fermenting process, the cleaned percolation water leaves the methane reactor as wastewater and is intermediately stored in the storage buffer tank and can be returned to the percolators from there.

In this way, a constant temperature can be maintained in the biogas reactor, if the biogas reactor preferably can be heated. The temperature can lie either at approximately 37° C. or at approximately 55° C.

In a preferred embodiment of the invention, the storage buffer tank can be aerated. This has the advantage that bacteria from the biogas reactor are killed, so that a seeding of the hydrolysis with methane bacteria and a production of biogas in the percolators can be excluded in this way.

An accumulation of the most varied substances in the wastewater can be avoided, if a part of the circuit water is withdrawn and fresh water is introduced.

In addition, the object of the invention is achieved by the use of the biogas plant for the production of biogas and for the storage of percolation liquid.

By mixing with air, biogas can easily lead to explosive mixtures; therefore, the production and storage is subjected to special safety regulations.

Such a risk of explosion can be very greatly reduced by the method according to the invention, since the percolators are based on an aerobic operating mode and thus the formation of methane is stopped. In addition, a storage of biogas is not necessary, since only the percolation liquid is stored.

The invention will be described in more detail below on the basis of a figure. Taken individually, FIG. 1 shows a schematic representation of a biogas plant according to the invention.

FIG. 1 shows a schematic representation of a biogas plant I for the production of biogas according to need.

Percolators 2 are constructed as in the Garagen method, i.e., they are built as a type of container or other space with an acid-resistant lining. They are configured in such a way that they are charged by the usual technological means (for example, with wheel loaders). The bottom and/or the walls are also equipped with sieve bottoms 3, so that a solid-liquid separation can occur at these sites. In order to avoid obstructions or in order to loosen the material, a shock of compressed air can be supplied discontinuously through these perforated walls. In other respects, percolators 2 operate at ambient pressure and an input of air is harmless and can also be provided continuously or discontinuously. The percolation liquid collects at the bottom or under the sieve bottom 3 and is sprayed continuously or discontinuously in the circuit over the biogenic material by means of one pump 4 for each percolator 2. The percolation liquid dissolves the acids and other substances that form on the solid bed. Therefore, the percolation liquid is enriched with easily fermentable substances.

Excess percolation liquid is pumped into the buffer tank 5 with appropriate filling level. Solid and/or suspended matter is optionally separated beforehand in separator 8. From there, the percolation liquid is pumped in a gas-tight manner into the biogas reactors 6 by means of pumps 40. These reactors function according to a reaction principle that is common for wastewater technology (UASB, sludge bed, solid bed reactor). The percolation liquid is fermented rapidly to biogas in the biogas reactors 6. The percolation liquid that is cleaned in this way is discharged as wastewater [from] biogas reactors 6 and is intermediately stored in storage buffer tank 7, before it is returned to percolators 2 as needed, and there allows the liquid level to rise. In this way, the liquid is always conducted in the circuit. An accumulation of different substances in the liquid is avoided, if a part of the circuit liquid is discharged discontinuously and fresh liquid (water) is introduced.

In addition to their storage function, the buffer tank 5 and the storage buffer tank 7 also serve as separators for sinking or floating substances, which are removed discontinuously. In addition, the possibility exists of separating other undesired substances from the individual buffer tanks 5 and/or storage buffer tanks 7 by use of high-power separators (for example, centrifuges).

The storage buffer tank 7 may also be ventilated as needed in order to promote further biological decomposition or the separation of undesired substances, such as ammonium, for example, in the storage buffer tank 7. The bacteria discharged from the bioreactor are also killed to the greatest extent by the aeration of the storage buffer tank 7, so that a seeding of hydrolysis by methane bacteria and thus a production of biogas in percolators 2 is excluded.

The biogas plant 1 can be driven according to the invention, in particular, in such a way that the aerobic percolation circuit and the anaerobic biogas production circuit can be strictly separated from one another. It is thus assured that a quantity of free biogas (methane) that would affect safety is not present in the region of percolators 2 and/or in the region of the storage buffer tank 7. This leads to an improved operational safety of the entire plant.

LIST OF REFERENCE NUMBERS

1 Biogas plant
2 Percolator
3 Sieve bottom
4 Pump
5 Buffer tank
6 Bioreactor
7 Storage buffer tank
8 Separator
40 Pump
A Wastewater
B Biogenic material
F Fresh water
L Air

The invention claimed is:

1. A method for decomposing biogenic material, wherein a percolator is loaded with biogenic material,
   a percolation liquid is separated through a sieve and again sprayed onto the biogenic material, without first being passed through a biogas-reactor,
   excess percolation liquid is introduced into a buffer tank, from there pumped into a biogas-reactor and fermented to biogas, wherein the cleaned percolation liquid is transferred as wastewater into a storage buffer tank and wherein the wastewater can be transferred from there again into the percolator.

2. The decomposing method according to claim 1, further characterized in that the excess percolation liquid is stored.

3. The decomposing method according to claim 1, further characterized in that a shock of compressed air is impressed discontinuously through the perforated walls of a sieve bottom.

4. The decomposing method according to claim 1, further characterized in that normal pressure prevails in percolator.

5. The decomposing method according to claim 1, further characterized in that percolator is driven aerobically.

6. The decomposing method according to claim 1, further characterized in that a part of the wastewater is discharged discontinuously and fresh liquid is introduced.

7. The decomposing method according to claim 1, further characterized in that sinking and/or floating substances are separated in buffer tank and/or in storage buffer tank.

8. The decomposing method according to claim 1, further characterized in that the fermenting to biogas is conducted by means of added and/or immobilized bacteria.

9. A biogas plant for a method according to claim 1, consisting of at least one percolator with a sieve bottom and a pump, a buffer tank, at least one biogas reactor, and at least one storage buffer tank.

10. The biogas plant according to claim 9, further characterized in that it consists of at least two parallelly connected percolators.

11. The biogas plant according to claim 9, further characterized in that the percolators are acid-resistant.

12. The biogas plant according to claim 9, further characterized in that the percolators are heatable.

13. The biogas plant according to claim 9, further characterized in that the biogas reactor is gas-tight.

14. The biogas plant according to claim 9, further characterized in that the biogas reactor is heatable.

15. The biogas plant according to claim 9, further characterized in that the storage buffer tank can be aerated.

16. A use of the biogas plant according to claim 9 for the production of biogas and for the storage of percolation liquid.

* * * * *